(12) United States Patent
Oomori et al.

(10) Patent No.: US 6,693,293 B2
(45) Date of Patent: Feb. 17, 2004

(54) SURFACE INSPECTION APPARATUS USING RADIATION OR LIGHT

(75) Inventors: Takeo Oomori, Hachioji (JP); Kazuhiko Fukazawa, Misato (JP)

(73) Assignee: Nikon Corporation, Tokyo (JP)

( * ) Notice: Subject to any disclaimer, the term of this patent is extended or adjusted under 35 U.S.C. 154(b) by 204 days.

(21) Appl. No.: 09/918,476

(22) Filed: Aug. 1, 2001

(65) Prior Publication Data

US 2002/0017620 A1 Feb. 14, 2002

(30) Foreign Application Priority Data

Aug. 4, 2000 (JP) ........................ 2000-236774
Jul. 16, 2001 (JP) ........................ 2001-215211

(51) Int. Cl.$^7$ ............................................. G01N 21/86
(52) U.S. Cl. .................. 250/559.4; 356/237.7; 250/559.42
(58) Field of Search ................ 250/559.4–559.49, 250/559.11, 559.22, 559.24, 559.26; 356/237.1–237.5

(56) References Cited

U.S. PATENT DOCUMENTS 5,963,328 A * 10/1999 Yoshida et al. .......... 356/237.2
6,512,578 B1 * 1/2003 Komatsu et al. ......... 356/237.5

FOREIGN PATENT DOCUMENTS

JP 8-5573 1/1996
JP 2000-28535 A 1/2000

OTHER PUBLICATIONS

U.S. patent application Ser. No. 09/083,538, Tawaka, filed May 22, 1998.
U.S. patent application Ser. No. 09/481,503, Komatsu et al, filed Jan. 12, 2000.
U.S. patent application Ser. No. 09/462,279, Komatsu et al, filed Feb. 22, 2000.

* cited by examiner

Primary Examiner—Thanh X. Luu
(74) Attorney, Agent, or Firm—Oliff & Berridge, PLC

(57) ABSTRACT

A surface inspection apparatus is constructed of an illumination unit for irradiating a wafer with illumination radiation for inspection, and a radiation receiving unit having a CCD imaging device for detecting an image of the wafer by converging regularly reflected radiation from the wafer. The wafer surface is inspected based on the image detected by the CCD imaging device. An incident angle i and a wavelength $\lambda$ of the use-for-inspection illumination radiation with which the illumination unit irradiates the wafer, are set to satisfy the following conditional formula:

$$\lambda/(\sin i+1) \leq p \qquad (1)$$

where p is a pattern repetitive pitch.

10 Claims, 6 Drawing Sheets

SURFACE INSPECTION APPARATUS USING RADIATION OR LIGHT

This application claims the benefit of Japanese Patent applications No. 2000-236774 and No. 2001-215211 which are hereby incorporated by reference.

BACKGROUND OF THE INVENTION

1. Field of the Invention

The present invention relates to a surface inspection apparatus for inspecting a surface of a wafer or the like in a process of manufacturing an IC chip, a liquid crystal display panel and so on.

2. Related Background Art

The IC chip and the liquid crystal display device panel are constructed by stacking a variety of different circuit patterns in a multi-layered structure on a wafer surface or the like. These circuit patterns are formed in a way that stacks the patterns layer by layer on the wafer by making use of a photolithography process and others. When forming these circuit patterns, if there are defects such as a scatter in thickness of a layer of resist for forming the circuit pattern, a flaw and so forth, this leads to an ill-manufactured product like the IC chip to be manufactured, and hence it is of much importance to inspect the surface in the manufacturing process.

The surface of the wafer or the like has hitherto been inspected by irradiating the wafer surface with a variety of illumination light from a variety of angles, wherein an observer directly visually observes the surface in a way that rotates or sways the inspection target wafer. Over the recent years, there has increasingly been a demand for automating the surface inspection in order to minimize a scatter in quality of the inspection, save a labor for the inspection and speed up the inspection. What was proposed under such circumstances, as disclosed in, for example, Japanese Patent Application Laid-Open Publication No.2000-28535, is a surface inspection apparatus, wherein the inspection target wafer surface is irradiated with use-for-inspection illumination radiation or light emitted from an illumination optical system, an imaging device receives regularly reflected radiation or light from the wafer surface and picks up an image of the wafer surface, and the apparatus inspects the wafer surface for a defect like a flaw and so forth by processing an image signal of the thus picked-up image.

By the way, according to this type of surface inspection apparatus, it is judged from an intensity of the regularly reflected radiation from the wafer surface whether the wafer surface is defective or not. The IC chip or the like provided on the wafer surface is formed by stacking repetitive patterns having fine pitches. When the wafer surface is irradiated with the use-for-inspection illumination radiation, there outgoes diffracted radiation corresponding to the repetitive pattern pitches. Therefore, the regularly reflected radiation decreases corresponding to an occurrence of the diffracted radiation, and the imaging device picks up the image of the wafer surface with an intensity corresponding to the thus decreased regularly reflected radiation.

In this case, if the pattern on the wafer surface is normal, the image based on the regularly reflected radiation containing the decrease in intensity that corresponds to the diffracted radiation occurred, is picked up. For instance, however, if the defect such as a defocus or the like occurs in the photolithography process for creating the pattern, as an intensity of the diffracted radiation from this defective portion is different from that of the diffracted radiation from a portion having a normal pattern, so is the intensity of the regularly reflected radiation. Then, in the surface inspection apparatus, the signal processing of the image picked up by the imaging device is executed, and it is checked whether there exists a portion exhibiting a different intensity of the regularly reflected radiation from a radiation intensity of the image of the normal pattern, thereby inspecting the surface for the defect caused by the defocus.

As explained above, according to the surface inspection apparatus using the regularly reflected radiation, it is required that not only the regularly reflected radiation but also the diffracted radiation be occurred from the use-for-inspection illumination radiation with which the pattern on the wafer surface is irradiated. The regularly reflected radiation from the wafer surface are, however, obtained normally from any angles. In contrast, the diffracted radiation occurs depending on a pattern pitch on the wafer surface, and an incident angle and a wavelength of the illumination radiation. The diffracted radiation cannot always be generated effectively at all times, and a problem is that the effective surface inspection cannot be attained as the case may be. Particularly when the pattern pitch is small, there arises the problem in which the diffracted radiation do not occur, and the effective surface inspection is hard to perform.

SUMMARY OF THE INVENTION

It is a primary object of the present invention, which was devised to obviate the problems described above, to provide a surface inspection apparatus capable of detecting, in the case of inspecting a wafer surface formed with a periodically repeated pattern, an image of the surface of the inspection target object on the basis of regularly reflected radiation or light from the surface of this inspection target object and thus inspecting the surface for a defect from a luminance of this image efficiently and simply.

To accomplish the above object, according to one aspect of the present invention, a surface inspection apparatus comprises an illumination optical system for irradiating an inspection target object having its surface formed with a periodically repeated pattern with illumination radiation or light for inspection, a converging optical system for converging regularly reflected radiation from the inspection target object, and an imaging device for detecting an image of the inspection target object by receiving the regularly reflected radiation or light converged by the converging optical system. The surface inspection apparatus inspects the surface of the inspection target object on the basis of the image of the inspection target object that is detected by the imaging device and an incident angle i and a wavelength $\lambda$ of the use-for-inspection illumination radiation or light with which the illumination optical system irradiates the inspection target object are set to satisfy the following formula:

$$\lambda/(\sin i+1) \leq p \tag{1}$$

where p is a pattern repetitive pitch.

If the incident angle i and the wavelength $\lambda$ of the use-for-inspection illumination radiation is set to satisfy the above formula (1) with respect to the repetitive pitch p of the pattern formed on the surface of the inspection target object, when the pattern is irradiated with the use-for-inspection illumination radiation, diffracted radiation invariably outgoes from the pattern. It is therefore feasible to effectively easily inspect the surface of the inspection target object on the basis of an intensity of the regularly reflected radiation or light.

The surface inspection apparatus may preferably further comprise a wavelength selection unit for restricting a wavelength band of the use-for-inspection illumination radiation in order to obtain the use-for-inspection illumination radiation having the wavelength λ satisfying the formula (1).

The illumination optical system may preferably have a discharge radiation or light source for emitting line spectrums. An inspection efficiency is enhanced by using the discharge radiation or light source having these line spectrums, i.e., an intensive output.

The illumination optical system may preferably have a radiation or light source for supplying ultraviolet rays of which a wavelength is equal to 400 nm or smaller, and at least the illumination optical system may be disposed in an inert gas atmosphere or in a vacuum. In the case of using the radiation or light source for supplying the ultraviolet-rays having the wavelength of 400 nm or smaller as the radiation or light source of the illumination radiation for inspection, the diffracted radiation can be generated effectively from the pattern having an extremely small pitch. Further, though the ultraviolet-rays react to substances in the air with the result that the substances might adhere to the lens to frost the illumination system, this problem can be restrained from arising by disposing the illumination optical system in the inert gas atmosphere or in the vacuum.

According to the present invention the contrivance is that the incident angle i and the wavelength λ of the use-for-inspection illumination radiation with which the illumination optical system irradiates the inspection target object are set to satisfy the above formula (1). Hence, when the pattern is irradiated with the use-for-inspection illumination radiation, diffracted radiation invariably outgoes from the pattern, and it is possible to effectively easily inspect the surface of the inspection target object on the basis of the intensity of the regularly reflected radiation.

Moreover, the surface inspection apparatus may preferably further comprise an image processing inspection device for obtaining an image of the surface of the inspection target object by processing an image signal given from the imaging device, and inspecting the surface of the inspection target object for its defect on the basis of the surface image. This makes it possible to easily obtain the auto surface inspection apparatus for automatically detecting the intensity of the regularly reflected radiation.

DESCRIPTION OF THE PREFERRED EMBODIMENTS

Figure 1:
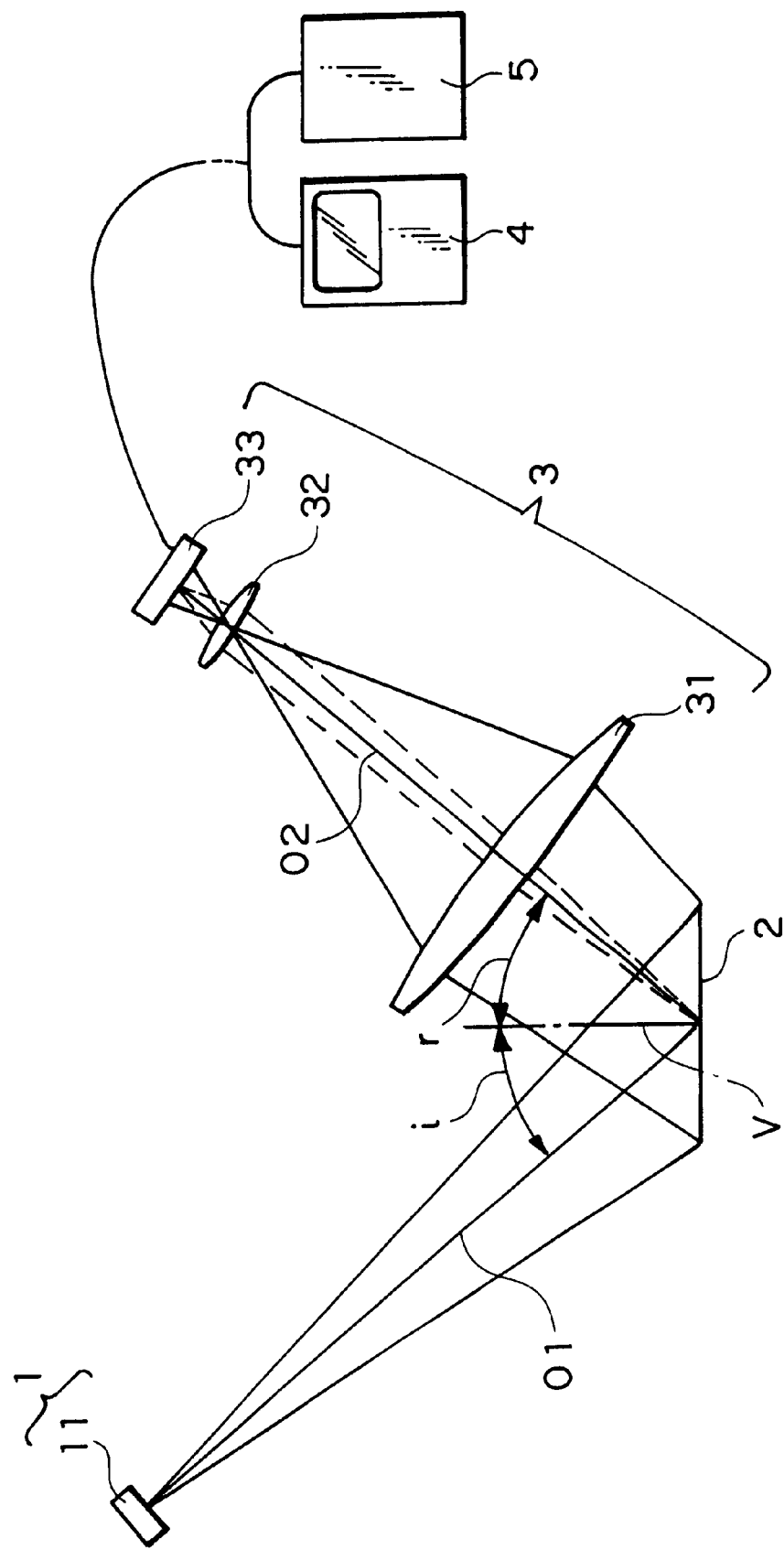
FIG. 1 is a schematic diagram showing a configuration of a surface inspection apparatus in a first embodiment of the present invention.

Preferred embodiments of the present invention will hereinafter be described with reference to the accompanying drawings. FIG. 1 shows a surface inspection apparatus in a first embodiment of the present invention. This apparatus is configured including a halogen lamp radiation source 11, and has an illumination unit (an illumination optical system) 1 for irradiating radiation ranging from 400 nm to a near infrared radiation range. The radiation emitted from the illumination unit 1 is incident upon the surface of a wafer 2, at which time an angle made by a normal line V perpendicular to the surface of the wafer 2 and by an optical axis O1 of the illumination radiation, is an incident angle i. When the surface of the wafer 2 is thus irradiated with the illumination radiation, the regularly reflected radiation from the surface of the wafer 2 outgoes at an exit angle r (=the incident angle i) to an optical axis O2. Further, the diffracted radiation outgoes from the surface of the wafer 2, corresponding to a pitch p of a pattern formed on the surface of the wafer 2, the incident angle i and a wavelength λ of the incident radiation. Note that an exit angle of the diffracted radiation at this time is in a direction different from the exit angle r of the regularly reflected radiation, and an intensity of the regularly reflected radiation corresponds to an intensity obtained by subtracting an intensity of the diffracted radiation from an intensity of the incident radiation.

A radiation receiving unit 3 is disposed facing to the regularly reflected radiation outgoing at the exit angle r as described above. The regularly reflected radiation from the surface of the wafer 2 enters the radiation receiving unit 3. The radiation receiving unit 3 is constructed of converging lenses 31, 32 (a converging optical system) and a CCD imaging element 33 (an imaging device). The regularly reflected radiation from the surface of the wafer 2 travels through the converging lenses 31, 32 and forms a surface image on the CCD imaging device 33. A signal of the image imaged by the CCD imaging device 33 is transmitted to a display unit 4 constructed of a CRT monitor, a liquid crystal display monitor, and so forth. The surface image is displayed on the display unit 4. This image signal is transmitted also to a processing unit 5.

Figure 2:
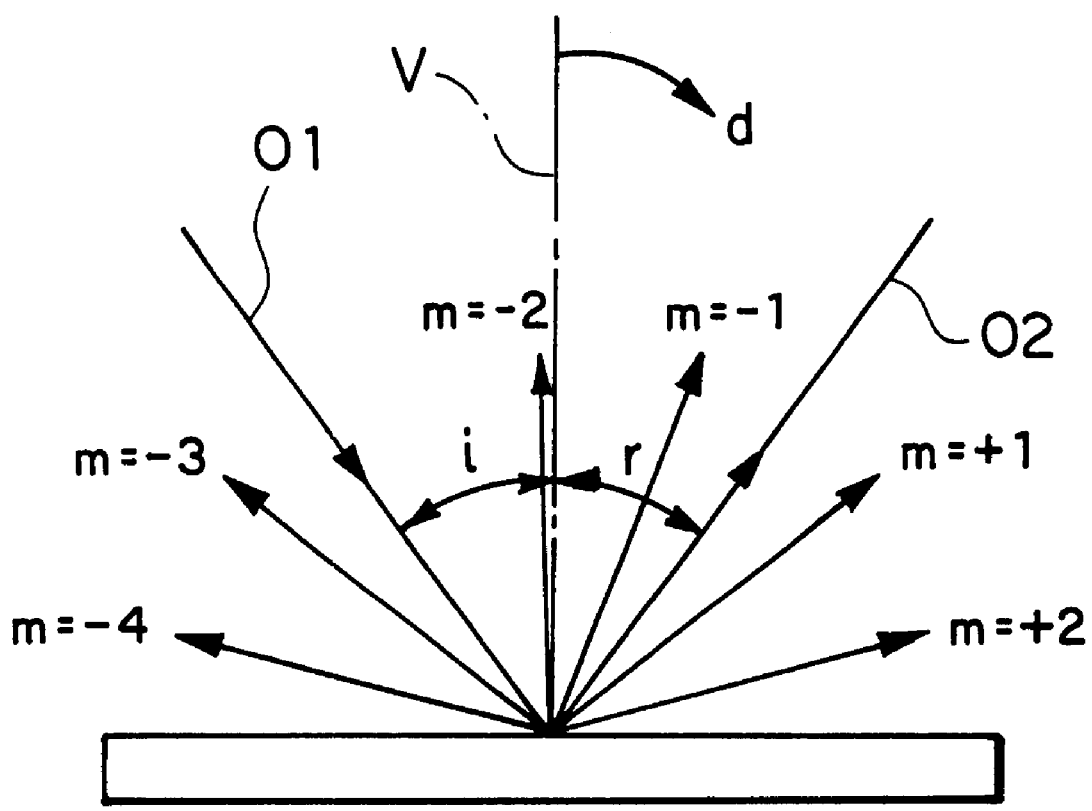
FIG. 2 is an explanatory diagram showing directions of regularly reflected radiation and diffracted radiation of illumination radiation falling upon a wafer.

Herein, as described above, when inspecting the surface of the wafer 2 on the basis of the regularly reflected radiation, it is required that the diffracted radiation be generated from the surface of the wafer 2, and a condition for generating the diffracted radiation will be explained referring to FIG. 2. FIG. 2 shows a case of where the illumination radiation being incident at the incident angle i with the optical axis O1 on the surface of the wafer 2 is regularly reflected therefrom, and outgoes at the exit angle r with the optical axis O2, wherein m-th order diffracted radiation (where m=1, 2, ..., and m=−1, −2, ...) outgoes as illustrated herein. Note that an exit angle d of the diffracted radiation is defined on the premise that angle in the right direction from the normal line V is positive in FIG. 2.

The following formula (2) is a conditional formula in which the m-th order diffracted radiation outgoes at the exit angle d:

$$\sin d - \sin i = m \cdot \lambda / p \qquad (2)$$

where p is the pattern pitch on the surface of the wafer and λ is the wavelength of the illumination radiation.

Herein, FIG. 2 illustrates the outgoing diffracted radiation up to (+) second order and down to (−) fourth order, however, there is a less occurrence in which the higher-order diffracted radiation outgoes in sequence as the exit angle d of the diffracted radiation becomes larger, with the result that only the (−) first order diffracted radiation outgoes. Hence, the condition that the (−) first order diffracted radiation outgoes, is the minimum condition under which the diffracted radiation outgoes, and this condition is considered as a basis. Therefore, it may be sufficient to satisfy a condition that the exit angle d of the (1) first order diffracted radiation is given such as −90°≦d as well as satisfying a condition such as −1≦sin d. If transformed by putting this condition into the above formula (2), the formula (3) is obtained. Note that this formula (3) is the same as the formula (1) described above.

$$\lambda/(\sin i+1) \leq p \qquad (3)$$

As understood from the discussion given above, when satisfying the conditional formula (3), it follows that the diffracted radiation occurs from the surface of the wafer 2, and the CCD imaging device 33 receives via the converging lenses 31, 32 the regularly reflected radiation having an intensity excluding the diffracted radiation. For example when the pattern pitch p=0.3 μm, if the incident angle i is equal to 19.5° or larger, there occurs the diffracted radiation with respect to the illumination radiation having the wavelength λ=400 nm or larger. Further, if the incident angle i=40°, there occurs the diffracted radiation with respect to the radiation having the wavelength λ=400 nm ~492 nm. If the incident angle i=60°, there occurs the diffracted radiation with respect to the radiation having the wavelength λ=400 nm ~560 nm. Thus, as the incident angle i is set larger, a possible-of-generating-the-diffracted-radiation wavelength range of the illumination radiation expands, and hence an inspection efficiency is enhanced.

Note that the radiation source 11 is not limited to the halogen lamp, i.e., an incandescent radiation source, and may involve the use of a metal halide lamp or the like as a discharge radiation source emitting the radiation having a wavelength of 400 nm or larger and exhibiting line spectrums. In the halogen lamp, a peak wavelength exists in a range of 700 nm or greater, and an output of the radiation having the wavelength in the vicinity of 400 nm is relatively weak. On the other hand, the metal halide lamp has an intensive output (emission line) in wavelengths of 436 nm and 546 nm and is therefore capable of more efficiently generating the diffracted radiation and exhibiting a high inspection efficiency.

Further, the radiation source 11 may also involve the use of a mercury lamp. The mercury lamp is a discharge radiation source for emitting the line spectrums. The mercury lamp outputs the radiation having wavelengths of 300 nm ~600 nm, and has the intensive output (emission line) in the wavelengths of 546 nm, 436 nm, 365 nm and 313 nm, thereby enhancing the inspection efficiency. The mercury lamp has much the line spectrums on the side of the short wavelengths, and hence the radiation or light quantity in the short wavelength range increases. The mercury lamp is effective particularly in the pattern of which the pitch is small. Especially under the above condition, i.e., the condition that the pattern pitch is 0.3 μm, and the incident angle is 60°, the diffracted radiation occurs with respect to the incident radiation having the wavelengths of 300 nm ~560 nm, and therefore the mercury lamp is suited under this condition.

According to the surface inspection apparatus shown in FIG. 1, the processing unit 5 linked to the CCD imaging device 33 processes the image signal obtained by the CCD imaging device 33, thereby performing the surface inspection. To be specific, an image, formed by the regularly reflected radiation, of the well-manufactured inspection target wafer 2 is measured and stored beforehand, and is compared with an image, formed by the regularly reflected radiation, of an actual inspection target wafer 2. Then, it is judged by doing pattern matching whether there is a difference between the two images, thus checking whether the surface has a defect or not. For example, if the inspection target wafer 2 has a defect such as a scatter in layer thickness caused by defocusing in the photolithography step, an intensity of the diffracted radiation at the defective spot is different from an intensity of the diffracted radiation from the well-manufactured wafer, and the intensities of the regularly reflected radiation differ from each other. Hence, this difference appears to be a difference in brightness at the defective spot, a difference in characteristic between the images, and so on. Whether the surface has the defect or not is judged based on a judgement as to whether there are the differences in brightness and in characteristic between those images.

Figure 3:
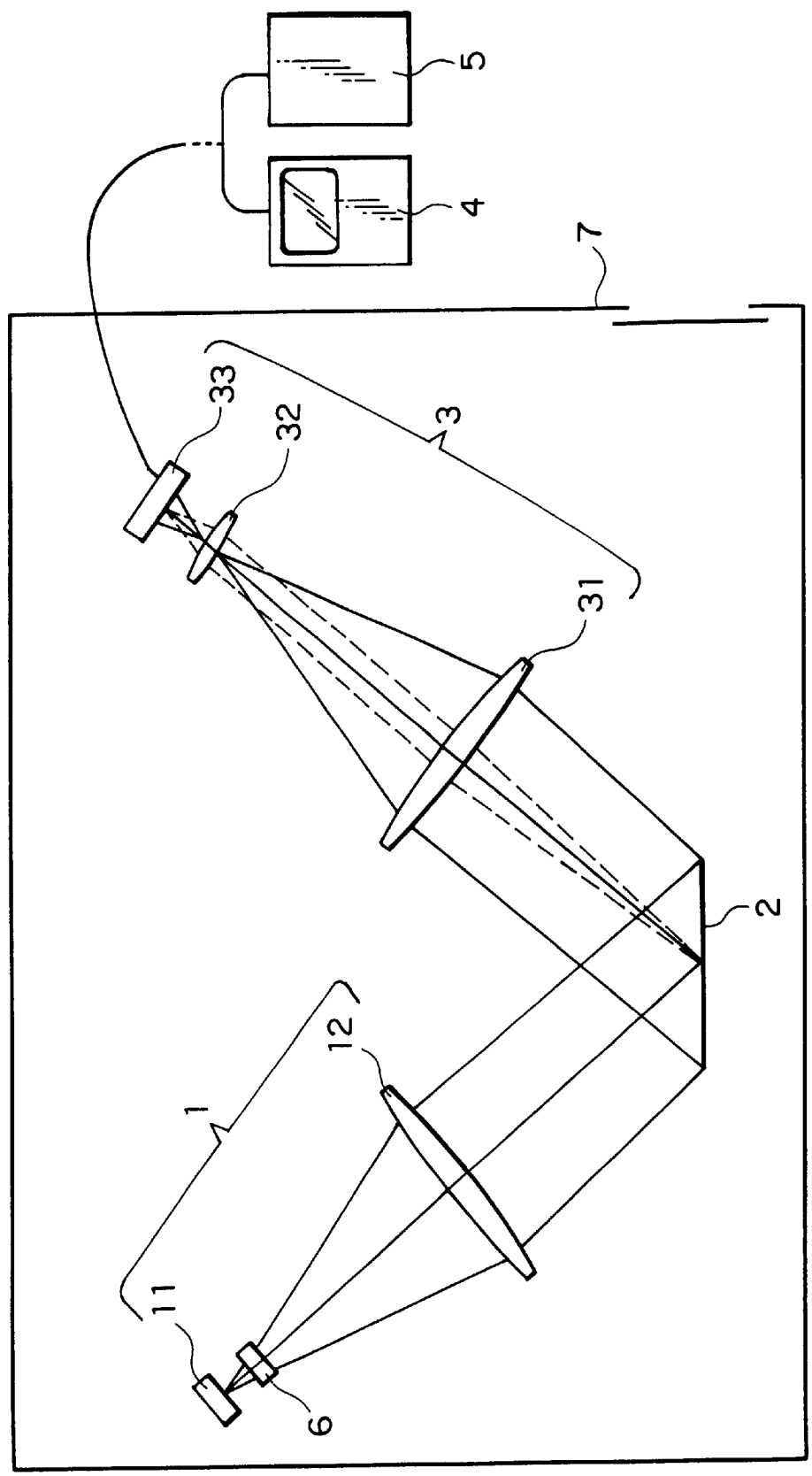
FIG. 3 is a schematic diagram showing a configuration of a surface inspection apparatus in a second embodiment of the present invention.

Next, the surface inspection apparatus in a second embodiment of the present invention will be described referring to FIG. 3. The same components of this inspection apparatus as those of the inspection apparatus constructed as shown in FIG. 1 are marked with the same numerals, and the repetitive explanations thereof are omitted. In this surface inspection apparatus, the illumination unit 1 is constructed of the mercury lamp as the radiation source 11 and an illumination lens 12. The illumination radiation emitted from the radiation source 11 are collimated by the illumination lens 12, and the collimated radiation flux impinges on the surface of the wafer 2. In this case, the incident angle i of the collimated flux impinging on the surface of the wafer 2 is uniform over the entire surface of the wafer 2. Accordingly, degrees of how much the reflected radiation and the diffracted radiation outgo, are uniform over the entire surface of the wafer 2, and sensitivities of detecting the defect on the surface are equalized.

Further, this surface inspection apparatus is provided with an unillustrated drive mechanism. This drive mechanism enables the illumination unit 1 and the radiation receiving unit 3 to turn about the axis extending through the center of the wafer 2 and perpendicular to the sheet surface, thereby making the incident angle i arbitrarily adjustable. This drive mechanism also makes arbitrarily adjustable a direction of the radiation receiving unit 3 so that this unit 3 is positioned in a direction of the exit angle of the regularly reflected radiation. Further, the incident angle i may be set arbitrarily adjustable by making the wafer 2 and either of the two units 1, 3 turnable through an angle about the axis of the wafer 2 instead of making both of the units 1, 3 turnable. If configured in this way, the condition of the incident angle can be set to such a point that there are much variations in the intensity of the diffracted radiation from the wafer 2, whereby the defect can be detected more precisely.

Note that the lenses 12, 31 may not be the convex lenses and may involve the use of reflecting optical elements such as a spherical reflecting mirror or the like, thereby making it feasible to downsize further the apparatus.

A wavelength selection unit 6 selects and lets the radiation pass therethrough, which exists in a wavelength range to generate the diffracted radiation among the radiations emitted from the radiation source 11. A variety of elements such as a dichroic mirror, an interference filter and others are prepared for the wavelength selection unit 6, and may be used interchangeably. With this configuration, the regularly reflected radiation received by the radiation receiving unit 3 become the radiation of which the diffracted radiation components are removed in all the wavelength ranges, thereby enhancing further the inspection efficiency.

In this surface inspection apparatus, the illumination unit 1, the wafer 2, the radiation receiving unit 3 and the wavelength selection unit 6 are housed in a chamber 7. An interior of the chamber is filled with an inert gas such as nitrogen, argon gas, and so on. This contrivance prevents the optical system from frosting due to the ultraviolet rays or the like of 400 nm or under. Note that the interior of the chamber 7 may be evacuated instead of filling it with the inert gas.

The surface inspection apparatus discussed above has been exemplified as the apparatus in which the processing unit 5 executes the image processing of the image signal obtained by the CCD imaging device 33, thereby detecting the defect on the surface. This surface inspection apparatus may also be used as a visual inspection system for inspecting the surface in a mode where an inspector observes the image on the display unit 4 or on a different monitor. The discussion given above has been focused on the case of taking in the image of the whole area of the wafer 2, however, an image of a part of the area of the wafer may be taken out, and the surface may be inspected in a way that relatively moves the wafer and the radiation flux.

Next, a method of determining the radiation source wavelength and the incident angle of the illumination unit 1 of the surface inspection apparatus in the first and second embodiments, will be explained with reference to FIGS. 4 through 6.

Figure 4:
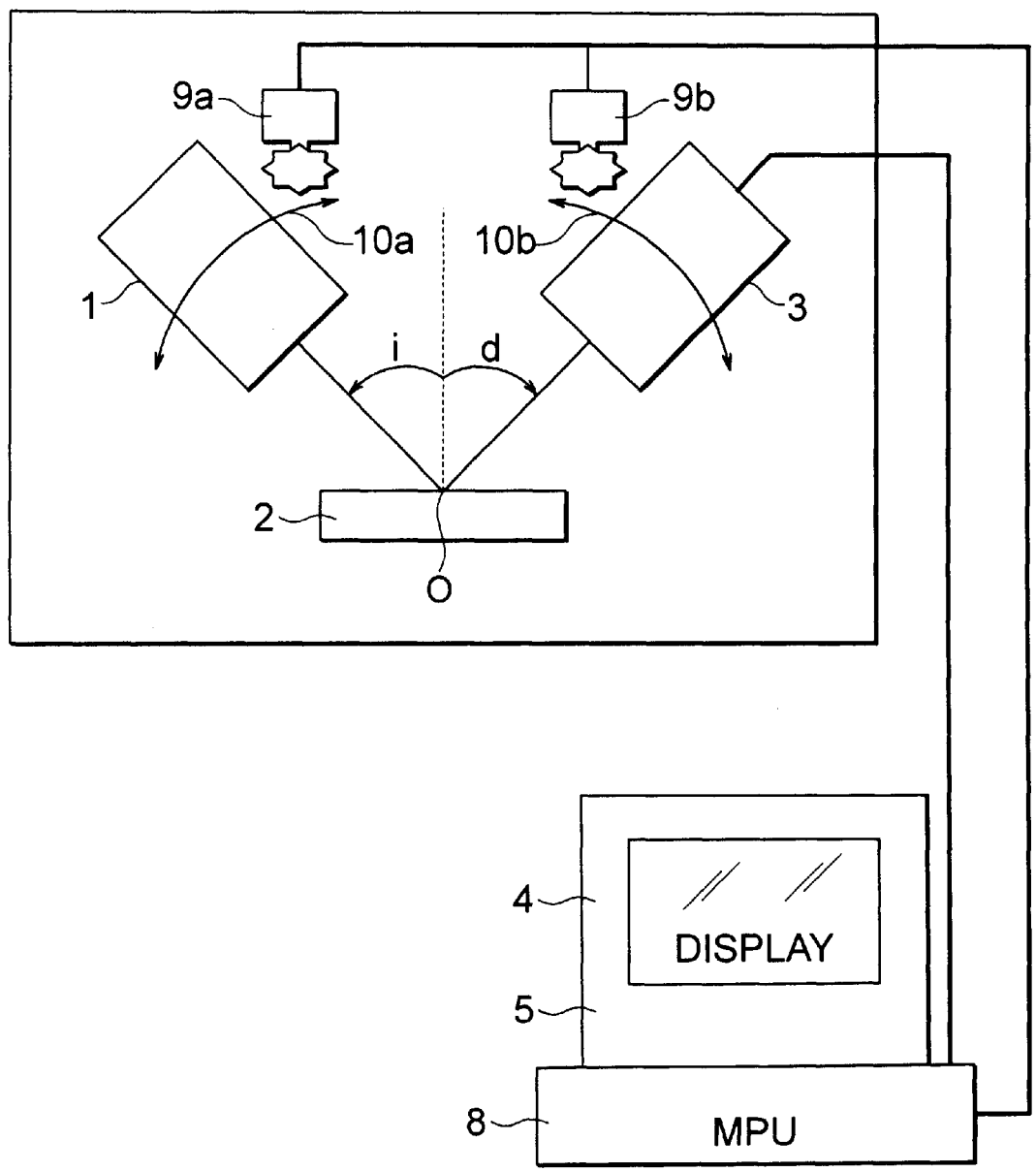
FIG. 4 is a schematic diagram showing a configuration of the surface inspection apparatus.

FIG. 4 is a schematic diagram showing a construction of the surface inspection apparatus. FIGS. 5 and 6 are control flowcharts showing how an MPU 8 determines the radiation source wavelength and the incident angle of the radiation from the illumination unit 1 of the surface inspection apparatus.

FIG. 4 basically illustrates the surface inspection apparatus in the first and second embodiments, however, some components are added. Referring to FIG. 4, the microprocessor unit (MPU) 8 controls the illumination unit 1 and the radiation receiving unit 3 so that the radiation receiving unit 3 is set in a direction of an exit angle d equal to the incident angle i of the illumination unit 1. The MPU 8 is assigned the whole control of the surface inspection apparatus, and controls the illumination unit 1, the radiation receiving unit 3, the display unit 4 and the processing unit 5.

The illumination unit 1 is moved by a drive source $9a$, and the radiation receiving unit 3 is moved by a drive source $9b$. These drive sources $9a$, $9b$ are subjected to drive control by the MPU 8. For instance, these drive sources are constructed of motors and driving mechanisms.

Further, in the illumination unit 1, for example, the halogen lamp, the metal halide lamp and the mercury lamp is selectively attached as the radiation source. An optimal radiation source is selected as the radiation source of the illumination unit 1 on the basis of the control flows shown in FIGS. 5 and 6, which will hereinafter be described.

The illumination unit 1 and the radiation receiving unit 3 include driving force transmission mechanisms $10a$, $10b$ for receiving the driving forces of the drive sources $9a$, $9b$, and are turnable about the axis O. The radiation receiving unit 3, as explained above, when the incident angle i of the illumination unit 1 changes, turns about the axis O corresponding to this change so that the radiation receiving unit 3 can receive the regularly reflected radiation from the wafer 2.

Figure 5:
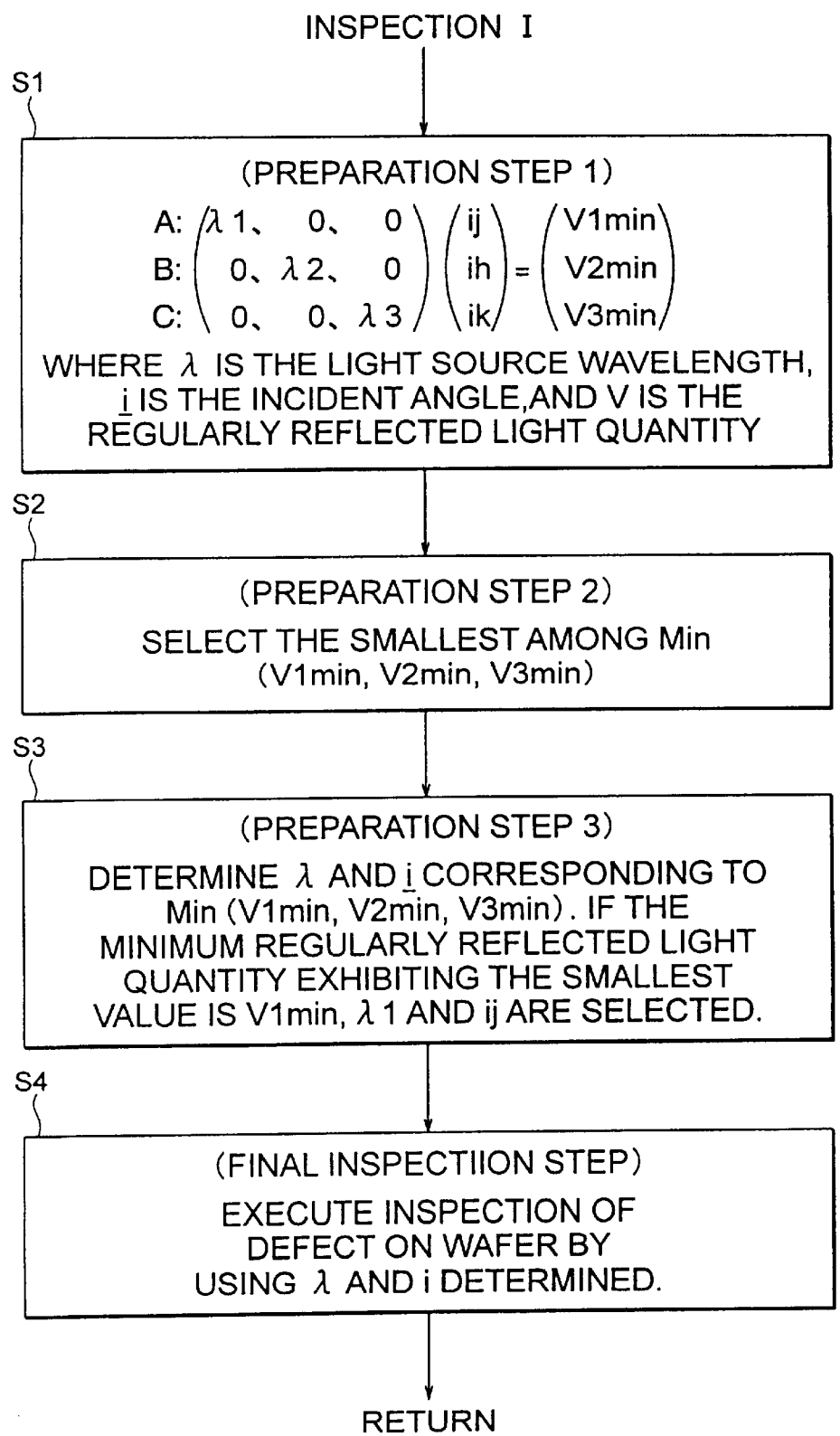
FIG. 5 is a control flowchart showing how a radiation or light source wavelength and an incident angle are determined.

FIG. 5 shows the control flow in which the MPU 8 determines the radiation source and the incident angle by measuring the regularly reflected radiation quantity V when changing the incident angle i for each of the radiation sources having different wavelengths such as the halogen lamp, the metal halide lamp and the mercury lamp.

Step S1 (preparation step 1): In the illumination unit 1, a radiation or light source A having a wavelength $\lambda 1$ is selected, and an incident angle ij is changed sequentially within a predetermined angular range. The MPU 8 changes the illumination unit 1 and the radiation receiving unit 3 sequentially within a predetermined range by controlling the drive sources $9a$, $9b$, and stores the memory unit with such an angular position ij as to obtain a minimum regularly reflected radiation quantity V1min. Namely, the MPU 8 detects the minimum regularly reflected radiation quantity by automatically calculating an average radiation quantity from the output of the CCD imaging device 33 of the radiation receiving unit 3 and, just when detecting the minimum regularly reflected radiation quantity, stores the wavelength $\lambda$ and the incident angle i in the memory unit.

The reason for detecting the minimum regularly reflected radiation quantity is that if a maximum regularly reflected radiation quantity is selected, there might be a possibility of storing an angular position in a state of containing no diffracted radiation component.

A method of detecting that the regularly reflected radiation quantity comes to its minimum is that the operator makes a visual confirmation on, e.g., a monitor of the display unit 4. There may also be taken a method, wherein just when the operator recognizes that the regularly reflected radiation quantity comes to its minimum, a storage indication switch is pressed in order to store the radiation or light source wavelength $\lambda$ and the incident angle i at that time.

Next, in the illumination unit 1, a radiation or light source B having a wavelength $\lambda 2$ is selected, and an incident angle ih is changed in sequentially within a predetermined angular range. Then, there is stored such an angular position ih as to obtain a minimum regularly reflected radiation quantity V2min.

Furthermore, in the illumination unit 1, a radiation or light source C having a wavelength $\lambda 3$ is selected, and an incident angle ik is changed in sequentially within a predetermined angular range. Then, there is stored such an angular position ik as to obtain a minimum regularly reflected radiation quantity V3min.

Note that the wafer used in the preparation step 1 may be, e.g., a first wafer among the wafers of lot for inspection, or a reference wafer representative of the wafers of lot for inspection may also be prepared.

Step S2 (preparation step 2): The smallest among the minimum regularly reflected radiation quantities V1min, V2min, and V3min obtained in the preparation step 1, is selected.

Step S3 (preparation step 3): A preparation step 3 is that the minimum regularly reflected radiation quantities are compared with each other, and the quantity exhibiting the smallest value among them is selected.

Supposing that the minimum regularly reflected radiation quantity exhibiting the smallest value is V1min, $\lambda 1$ and ij corresponding to this quantity V1min are selected.

Step S4 (final inspection step): The wafer is inspected for its defect by use of the predetermined radiation or light source wavelength $\lambda$ (e.g., $\lambda 1$) and the incident angle i (e.g., ij) that have been selected in the preparation step 3.

Note that in the final inspection step, the wafers of the inspection target lot are inspected by using the radiation source wavelength $\lambda$ and the incident angle i obtained in the preparation steps 1–3 described above. Then, a next lot of the wafers containing different pattern pitches P are likewise subjected to the processing in the preparation steps from the beginning and then the processing in the final inspection step.

Figure 6:
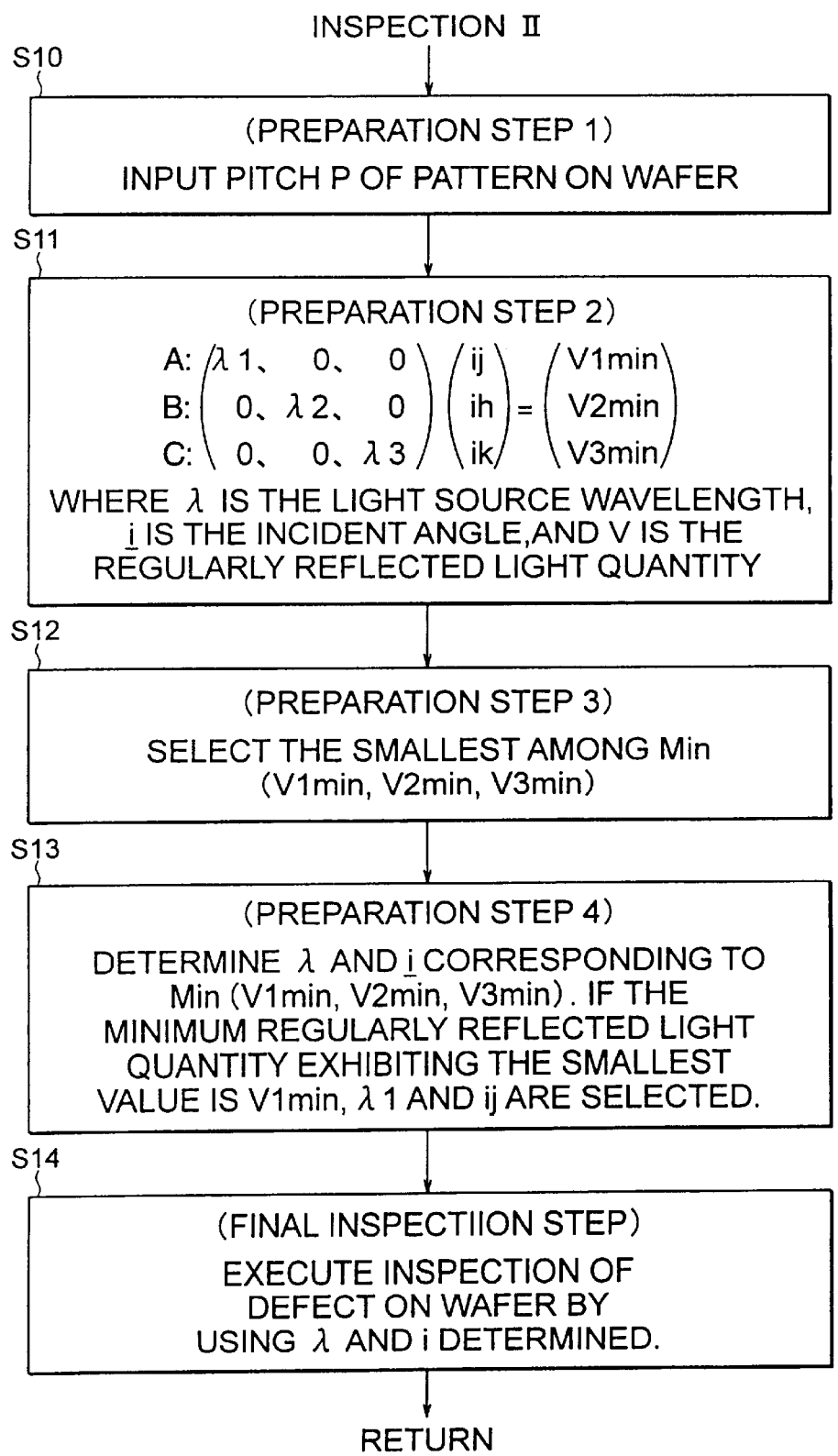
FIG. 6 is another control flowchart showing how the radiation or light source wavelength and the incident angle are determined.

FIG. 6 is an explanatory control flow showing a method different from the above method of determining the radiation or light source wavelength and the position of the incident angle explained in FIG. 5. The control flow in FIG. 6 is different from the control flow in FIG. 5 in terms of determining an incident angle variation range based on the formula 3 because of the pattern pitch P of the inspection target wafer being previously known. This control flow will hereinafter be explained.

Step S10 (preparation step 1): The pattern pitch P of the inspection target wafer is inputted. The MPU 8 automatically obtains data of the pattern pitch P of the wafer or obtains the data of the pattern pitch P that are inputted by the operator through a keyboard.

Step S11 (preparation step 2): What is executed in step 11 is substantially the same as step S1 in the preparation step 1 in FIG. 5, however, only different point is that the incident angle variation range of the radiation or light source is predetermined by the conditional formula 3. Namely, the pattern pitch P is inputted in step S10, whereby the incident angle i is thereby determined by the conditional formula such as $\lambda/(\sin i+1) \leq P$. This incident angle i is sequentially changed within the range that meets the conditional formula, and it follows that the MPU 8 stores the radiation or light source wavelength $\lambda$ and the angular position i in which to obtain the minimum regularly reflected radiation quantity.

Step S12: (preparation step 3): What is executed in this step S12 is the same as step S2 in FIG. 5.

Step S13: (preparation step 4): What is executed in this step S13 is the same as step S3 in FIG. 5.

Step S14: (final inspection step): What is executed in this step S14 is the same as step S4 in FIG. 5.

Note that the wavelength $\lambda$ and the incident angle i are determined by detecting the minimum regularly reflected radiation quantity in the preparation step in FIGS. 5 and 6, however, the determining method is not limited to this, and, since it is sufficient to be set in an incident angle position embracing the diffracted radiation, for example, there may also be taken an incident angle position corresponding to a regularly reflected radiation quantity exhibiting an intermediate value between the maximum regularly reflected radiation quantity and the minimum regularly reflected radiation quantity.

What is claimed is:

1. A surface inspection apparatus comprising:
   illumination optical system for irradiating an inspection target object having its surface formed with a periodically repeated pattern with radiation for inspection;
   converging optical system for converging regularly reflected radiation from said inspection target object; and
   imaging device for detecting an image of said inspection target object by receiving the regularly reflected radiation converged by said converging optical system,
   wherein said surface inspection apparatus inspects the surface of said inspection target object on the basis of the image of said inspection target object that is detected by said imaging device, and
   an incident angle i and a wavelength $\lambda$ of a use-for-inspection illumination radiation with which said illumination optical system irradiates said inspection target object, are set to satisfy the following formula:

$$\lambda/(\sin i+1) \leq p$$

where p is a pattern repetitive pitch.

2. A surface inspection apparatus according to claim 1, further comprising a wavelength selection unit for restricting a wavelength band of the use-for-inspection illumination radiation.

3. A surface inspection apparatus according to claim 1, wherein said illumination optical system has a discharge radiation source for emitting line spectrums.

4. A surface inspection apparatus according to claim 2, wherein said illumination optical system has a radiation source for supplying ultraviolet rays of which a wavelength is equal to 400 nm or smaller, and
   at least said illumination optical system is disposed in an inert gas atmosphere or in a vacuum.

5. A surface inspection apparatus according to claim 1, further comprising an image processing inspection device or obtaining an image of the surface of said inspection target object by processing an image signal given from said imaging device, and inspecting the surface of said inspection target object for its defect on the basis of the surface image.

6. A surface inspection apparatus according to claim 1, further comprising:
   illumination unit driving means for driving an illumination unit constituting said illumination optical system;
   radiation receiving unit driving means for driving a radiation receiving unit constructed of said converging optical system and said imaging device; and
   control means for controlling said illumination unit driving means and said radiation receiving unit driving means, and controlling said radiation receiving unit so that said radiation receiving unit is positioned in an outgoing direction of the regularly reflected radiation that changes corresponding to a change in the incident angle of a use-for-inspection illumination radiation emitted from said illumination unit.

7. A surface inspection method used for a surface inspection apparatus comprising:
   at least two pieces of first and second use-for-inspection radiation sources each having a different wavelength of illumination radiation;
   a converging optical system for converging regularly reflected radiation from an inspection target object having its surface irradiated with said first and second use-for-inspection radiation source and formed with a periodically repeated pattern; and
   an imaging device for detecting an image of said inspection target object by receiving the regularly reflected radiation converged by said converging optical system, said surface inspection apparatus inspecting the surface of said inspection target object on the basis of the image of said inspection target object which is detected by said imaging device,
   said method comprising:
   a first imaging step of executing an imaging process based on the regularly reflected radiation by said imaging device in a way that sequentially changes an angle of said first use-for-inspection radiation source within a predetermined incident angle range;
   a first storing step of storing such an angular position as to obtain a first predetermined regularly reflected radiation quantity by receiving the regularly reflected radiation in said first imaging step;
   a second imaging step of executing the imaging process based on the regularly reflected radiation by said imaging device in a way that sequentially changes an angle of said second use-for-inspection radiation source within a predetermined incident angle range;
   a second storing step of storing such an angular position as to obtain a second predetermined regularly reflected radiation quantity by receiving the regularly reflected radiation in said second imaging step;

a comparing step of comparing the first predetermined regularly reflected radiation quantity in said first storing step with the second predetermined regularly reflected radiation quantity in said second storing step; and a selecting step of selecting, based on a compared result in said comparing step, one of the angular positions stored in said first and second storing steps, and selecting one of said first and second use-for-inspection radiation sources used for obtaining the selected angular position.

8. A surface inspection method according to claim 7, wherein the first and second regularly reflected radiation quantities are minimum regularly reflected radiation quantities, and the angular position corresponding to the smaller of the first and second regularly reflected radiation quantities, is selected in said selecting step.

9. A surface inspection method used for a surface inspection apparatus comprising:

at least two pieces of first and second use-for-inspection radiation sources each having a different wavelength of illumination radiation;

a converging optical system for converging regularly reflected radiation from an inspection target object having its surface irradiated with said first and second use-for-inspection radiation source and formed with a periodically repeated pattern; and an imaging device for detecting an image of said inspection target object by receiving the regularly reflected radiation converged by said converging optical system, said surface inspection apparatus inspecting the surface of said inspection target object on the basis of the image of said inspection target object which is detected by said imaging device, said method comprising:

an inputting step of inputting a pitch of the periodic pattern;

a first imaging step of executing an imaging process based on the regularly reflected radiation by said imaging device in a way that sequentially changes an angle within such a range that an incident angle i of said first use-for-inspection radiation source satisfies the formula such as $\lambda 1/(\sin i+1) \leq P$ on the basis of the pitch P inputted in said inputting step and a wavelength $\lambda 1$ of said first use-for-inspection radiation source;

a first storing step of storing such an angular position as to obtain a first predetermined regularly reflected radiation quantity by receiving the regularly reflected radiation in said first imaging step;

a second imaging step of executing an imaging process based on the regularly reflected radiation by said imaging device in a way that sequentially changes an angle within such a range that an incident angle i of said second use-for-inspection radiation source satisfies the formula such as $\lambda 2/(\sin i+1) \leq P$ on the basis of the pitch P inputted in said inputting step and a wavelength $\lambda 2$ of said second use-for-inspection radiation source;

a second storing step of storing such an angular position as to obtain a second predetermined regularly reflected radiation quantity by receiving the regularly reflected radiation in said second imaging step;

a comparing step of comparing the first predetermined regularly reflected radiation quantity in said first storing step with the second predetermined regularly reflected radiation quantity in said second storing step; and a selecting step of selecting, based on a compared result in said comparing step, one of the angular positions stored in said first and second storing steps, and selecting one of said first and second use-for-inspection radiation sources used for obtaining the selected angular position.

10. A surface inspection method according to claim 9, wherein the first and second regularly reflected radiation quantities are minimum regularly reflected radiation quantities, and the angular position corresponding to the smaller of the first and second regularly reflected radiation quantities, is selected in said selecting step.

* * * * *